(12) United States Patent
Laredo

(10) Patent No.: US 8,262,947 B2
(45) Date of Patent: *Sep. 11, 2012

(54) UV/VISIBLE LIGHT ABSORBERS FOR OPHTHALMIC LENS MATERIALS

(75) Inventor: Walter R. Laredo, Fort Worth, TX (US)

(73) Assignee: Novartis AG, Basel (CH)

( * ) Notice: Subject to any disclaimer, the term of this patent is extended or adjusted under 35 U.S.C. 154(b) by 58 days.

This patent is subject to a terminal disclaimer.

(21) Appl. No.: 12/830,087

(22) Filed: Jul. 2, 2010

(65) Prior Publication Data

US 2011/0004301 A1  Jan. 6, 2011

Related U.S. Application Data

(60) Provisional application No. 61/223,251, filed on Jul. 6, 2009.

(51) Int. Cl.
*G02B 5/23* (2006.01)
*G02C 7/02* (2006.01)
*A61K 31/74* (2006.01)
*C07D 249/04* (2006.01)
*C07D 249/16* (2006.01)
*C07D 403/00* (2006.01)
*C09K 3/00* (2006.01)

(52) U.S. Cl. .............. 252/586; 252/183.11; 351/159; 424/78.04; 514/912; 523/107; 548/255; 548/257; 548/259; 548/260; 548/261; 623/6.11

(58) Field of Classification Search ............. 252/586, 252/183.11; 523/105, 106, 107; 526/320; 534/843, 852; 548/259, 261, 260, 255, 257; 623/6.11; 351/159; 424/78.04; 514/912

See application file for complete search history.

(56) References Cited

U.S. PATENT DOCUMENTS

| | | | |
|---|---|---|---|
| 4,611,061 A * | 9/1986 | Beard et al. | 548/260 |
| 5,280,892 A | 1/1994 | Smith | |
| 5,331,073 A | 7/1994 | Weinschenk, III et al. | |
| 5,470,932 A | 11/1995 | Jinkerson | |
| 5,693,095 A | 12/1997 | Freeman et al. | |
| 6,528,602 B1 | 3/2003 | Freeman et al. | |
| 6,806,337 B2 | 10/2004 | Schlueter et al. | |
| 6,846,897 B2 | 1/2005 | Salamone et al. | |
| 6,852,793 B2 | 2/2005 | Salamone et al. | |
| 6,872,793 B1 | 3/2005 | Schlueter | |
| 7,037,954 B2 | 5/2006 | Baba et al. | |
| 7,067,602 B2 | 6/2006 | Benz et al. | |
| 7,101,949 B2 | 9/2006 | Salamone et al. | |
| 7,691,918 B2 | 4/2010 | Jinkerson et al. | |
| 7,728,051 B2 | 6/2010 | Weinschenk et al. | |
| 2006/0197067 A1 * | 9/2006 | Xia et al. | 252/582 |
| 2007/0092830 A1 | 4/2007 | Lai et al. | |
| 2007/0092831 A1 | 4/2007 | Lai et al. | |
| 2008/0242818 A1 | 10/2008 | Benz et al. | |
| 2008/0266519 A1 | 10/2008 | Schlueter | |
| 2009/0043105 A1 | 2/2009 | Weinschenk et al. | |
| 2009/0088544 A1 | 4/2009 | Laredo | |
| 2009/0093604 A1 | 4/2009 | Schlueter | |
| 2009/0132039 A1 | 5/2009 | Cordova et al. | |
| 2009/0137745 A1 | 5/2009 | Cordova et al. | |
| 2010/0012589 A1 | 1/2010 | Jinkerson | |
| 2010/0113641 A1 | 5/2010 | Laredo | |
| 2011/0266505 A1 * | 11/2011 | Laredo et al. | 252/586 |

FOREIGN PATENT DOCUMENTS

| | | |
|---|---|---|
| CN | 1727338 A | 2/2006 |
| EP | 0131468 A2 | 1/1985 |
| EP | 0708108 A1 | 12/1997 |
| JP | 2005053058 A | 3/2005 |
| JP | 2009013148 A | 1/2009 |
| WO | WO2007050394 A2 | 5/2007 |
| WO | WO2008048880 A2 | 4/2008 |

OTHER PUBLICATIONS 2,4-Di-tert-butyl-6-(5-chloro-2H-benzotriazol-2-yl)phenol, 98%, Sigma-Aldrich Co., Catalog #423327.
International Search Report dated Dec. 22, 2010 for Patent Cooperation Treaty Application No. PCT/US2010/040972.

* cited by examiner

*Primary Examiner* — Bijan Ahvazi
(74) *Attorney, Agent, or Firm* — Patrick M. Ryan

(57) ABSTRACT

Benzotriazole UV/Visible light-absorbing monomers are disclosed. The UV/Vis absorbers are particularly suitable for use in intraocular lens materials.

19 Claims, 2 Drawing Sheets

UV/VISIBLE LIGHT ABSORBERS FOR OPHTHALMIC LENS MATERIALS

This application claims priority from U.S. Patent Application Ser. No. 61/223,251 filed Jul. 6, 2009.

FIELD OF THE INVENTION

This invention is directed to ultraviolet/visible light absorbers. In particular, this invention relates to novel benzotriazole monomers especially suitable for use in implantable ophthalmic lens materials.

BACKGROUND OF THE INVENTION

Many ultraviolet and visible light absorbers are known as ingredients for polymeric materials used to make ophthalmic lenses. Such absorbers are preferably covalently bound to the polymeric network of the lens material instead of simply physically entrapped in the material to prevent them from migrating, phase separating or leaching out of the lens material. Such stability is particularly important for implantable ophthalmic lenses where the leaching of the absorber may present both toxicological issues and lead to the loss of UV/visible blocking activity in the implant.

Numerous copolymerizable benzatriazole, benzophenone and triazine absorbers are known. Most of these compounds are known as UV absorbers, though some may be known to also absorb some portion of visible light. Many absorbers contain conventional olefinic polymerizable groups, such as methacrylate, acrylate, methacrylamide, acrylamide or styrene groups. Copolymerization with other ingredients in the lens materials, typically with a radical initiator, incorporates the absorbers into the resulting polymer chain. Incorporation of additional functional groups on an absorber may influence one or more of the absorber's light-absorbing properties, solubility or reactivity. If the absorber does not have sufficient solubility in the remainder of the ophthalmic lens material ingredients or polymeric lens material, the absorber may coalesce into domains that could interact with light and result in decreased optical clarity of the lens.

Examples of polymeric ophthalmic lens materials that incorporate UV absorbers can be found in U.S. Pat. Nos. 5,290,892; 5,331,073 and 5,693,095.

SUMMARY OF THE INVENTION

The present invention provides benzotriazole light absorbing monomers that absorb both ultraviolet light and a portion of visible light ("UV/Vis absorbers"). These absorbers are suitable for use in ophthalmic lenses, including contact lenses. They are particularly useful in implantable lenses, such as intraocular lenses (IOLs).

The absorber compounds of the present invention absorb wavelengths of light between 400-450 nm in addition to higher energy UVA rays between 400-320 nm, UVB rays between 320-280 nm, and UVC rays below 280 nm. They contain reactive groups, which allow for covalent attachment of the absorbers to ocular lens materials. Additionally, the absorbers of the present invention can be synthesized in approximately 4-6 steps from readily available starting materials.

The present invention also relates to ophthalmic device materials containing such UV/Vis absorbers.

DETAILED DESCRIPTION OF THE INVENTION

Figure 1:
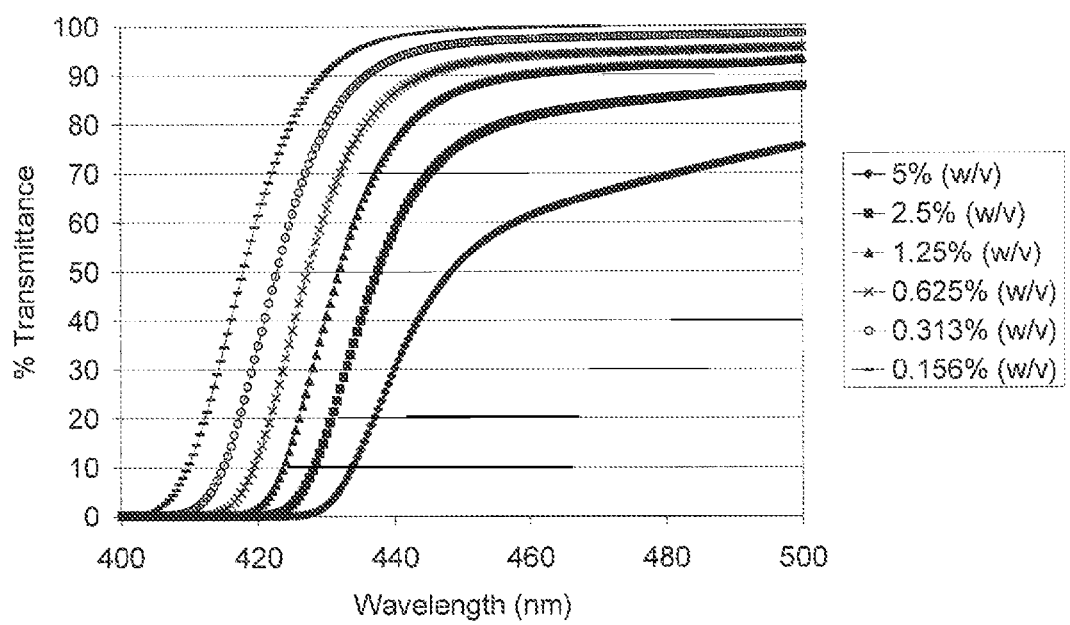
FIG. 1 shows percent transmittance curves for the UV/Vis is absorber Compound 2 at various concentrations.

Unless indicated otherwise, all ingredient amounts expressed in percentage terms are presented as % w/w.

The UV/Vis is absorbers of the present invention have the structure

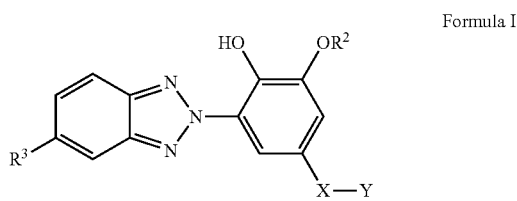

Formula I wherein
$X = C_3$-$C_4$ alkenyl, $C_3$-$C_4$ alkyl, $CH_2CH_2CH_2SCH_2CH_2$ or $CH_2CH_2CH_2SCH_2CH_2CH_2$;
Y=nothing if $X = C_3$-$C_4$ alkenyl, otherwise
$Y = $ —O—C(=O)—C($R^1$)=$CH_2$, —O—C(=O)NHCH$_2$CH$_2$OC(=O)—C($R^1$)=$CH_2$, or —O—C(=O)NHC(CH$_3$)$_2$(C$_6$H$_4$)C(CH$_3$)=$CH_2$;
$R^1$=H, $CH_3$, $CH_2CH_3$, or $CH_2OH$;
$R^2 = C_1$-$C_4$ alkyl; and
$R^3$=H, $CH_3$, $CH_3O$, F, Cl, Br, I, or $CF_3$.

Preferably, the UV/Vis is absorbers of the present invention are those wherein
$X = C_3$-$C_4$ alkenyl, $C_3$-$C_4$ alkyl, or $CH_2CH_2CH_2SCH_2CH_2$;
Y=nothing if $X = C_3$-$C_4$ alkenyl, otherwise $Y = $ —O—C(=O)—C($R^1$)=$CH_2$;
$R^1$=H or $CH_3$;
$R^2 = C_1$-$C_2$ alkyl; and
$R^3 = CH_3$, $CH_3O$, F, Cl, or $CF_3$.

Three preferred absorbers of the present invention are:

2-(3-(3-(5-chloro-2H-benzo[d][1,2,3]triazol-2-yl)-4-hydroxy-5-methoxy-phenyl)propylthio)ethyl methacrylate ("Compound 1");

4-allyl-2-(5-chloro-2H-benzo[d][1,2,3]triazol-2-yl)-6-methoxyphenol ("Compound 2");

3-(3-(5-chloro-2H-benzo[d][1,2,3]triazol-2-yl)-4-hydroxy-5-methoxy-phenyl)propyl methacrylate ("Compound 3");

4-allyl-2-methoxy-6-(5-(trifluoromethyl)-2H-benzo[d][1,2,3]triazol-2-yl)phenol ("Compound 4"); and 3-(4-hydroxy-3-methoxy-5-(5-(trifluoromethyl)-2H-benzo[d][1,2,3]triazol-2-yl)phenyl)propyl methacrylate ("Compound 5").

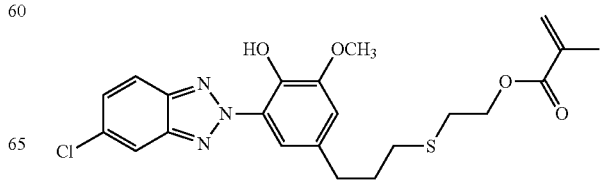

Compound 1

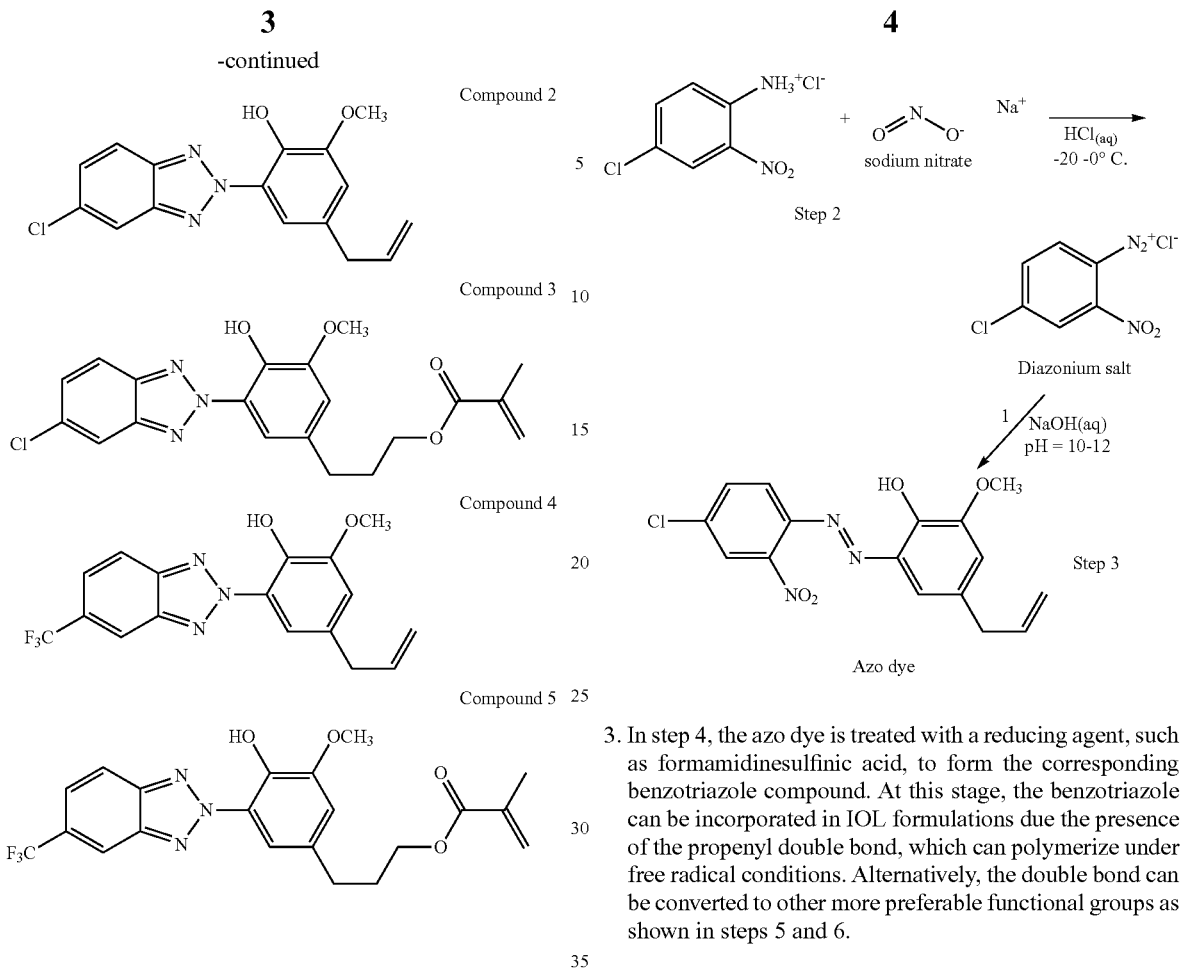

The synthesis of the UV/Vis is absorbers of the present invention is described below.

1. The UV absorbers are synthesized in 4-6 steps. In Step 1, the phenol derivative 1 is synthesized via the hydroxymethylation of eugenol, an inexpensive starting material derived from essential oils such as clove is oil, nutmeg, cinnamon, and bay leaf.

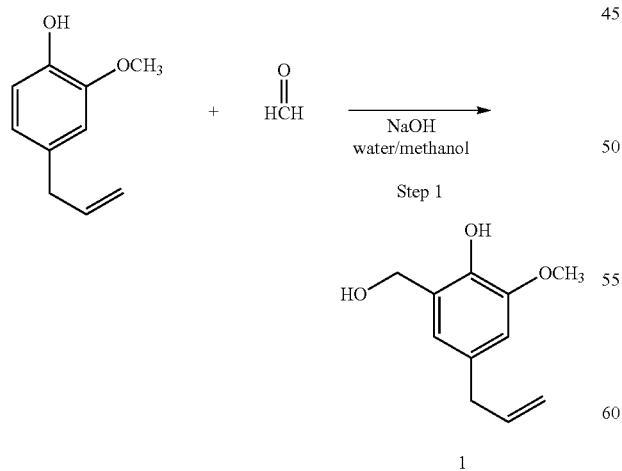

2. In steps 2 and 3, the diazonium salt of a 2-nitroaniline derivative is prepared and subsequently reacted with 1 to form an azo dye.

3. In step 4, the azo dye is treated with a reducing agent, such as formamidinesulfinic acid, to form the corresponding benzotriazole compound. At this stage, the benzotriazole can be incorporated in IOL formulations due the presence of the propenyl double bond, which can polymerize under free radical conditions. Alternatively, the double bond can be converted to other more preferable functional groups as shown in steps 5 and 6.

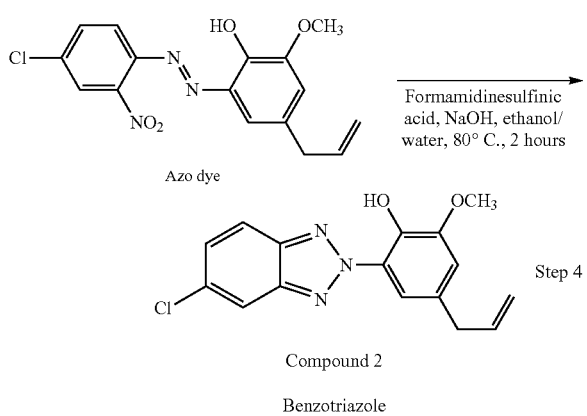

4. The benzotriazole from step 4 can be further reacted as shown in steps 5 and 6 to form an intermediate that contains hydroxyl groups which can then be esterified to contain (meth)acrylate groups. The incorporation of hydroxyl groups can be carried out using a wide range of synthetic methodologies, including Michael Addition using mercaptans or hydroboration/oxidation using boron containing compounds such as borane-methyl sulfide complexes. The resulting hydroxyl groups can then be converted to polymerizable (meth)acrylate groups. The (meth)acrylate groups can then form covalent bonds when reacted with vinyl monomers, co-monomers, macromers, crosslinking agents, and other components typically used in making polymer-based ocular materials, particularly acrylics.

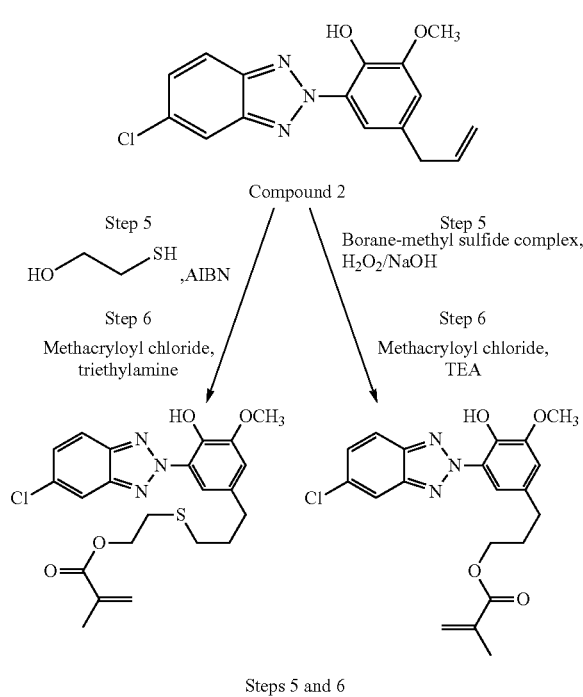

Steps 5 and 6

The UV/Vis is absorbers of the present invention are particularly suitable for use in IOLs. IOL materials will generally contain from 0.1 to 5% (w/w) of a UV/Vis is absorber of the present invention. Preferably, IOL materials will contain from 0.5 to 4% (w/w) of an absorber of the present invention. Most preferably, IOL materials will contain from 1 to 3% (w/w) of an absorber of the present invention. Such device materials are prepared by copolymerizing the absorbers of the present invention with other ingredients, such as device-forming materials, cross-linking agents, and optionally blue-light blocking chromophores.

Many device-forming monomers are known in the art and include both is acrylic and silicone-containing monomers among others. See, for example, U.S. Pat. Nos. 7,101,949; 7,067,602; 7,037,954; 6,872,793 6,852,793; 6,846,897; 6,806,337; 6,528,602; and 5,693,095. In the case of IOLs, any known IOL device material is suitable for use in the compositions of the present invention. Preferably, the ophthalmic device materials comprise an acrylic or methacrylic device-forming monomer. More preferably, the device-forming monomers comprise a monomer of formula IV:

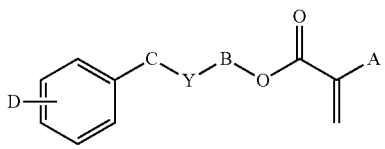

IV where in formula IV:
A is H, $CH_3$, $CH_2CH_3$, or $CH_2OH$;
B is $(CH_2)_m$ or $[O(CH_2)_2]_z$;
C is $(CH_2)_w$;
m is 2-6;
Z is 1-10;
Y is nothing, O, S, or NR', provided that if Y is O, S, or NR', then B is $(CH_2)_m$;

R' is H, $CH_3$, $C_nH_{2n'+1}$ (n'=1-10), iso-$OC_3H_7$, $C_6H_5$, or $CH_2C_6H_5$;
w is 0-6, provided that m+w≦8; and
D is H, $C_1$-$C_4$ alkyl, $C_1$-$C_4$ alkoxy, $C_6H_5$, $CH_2C_6H_5$ or halogen.

Preferred monomers of formula IV are those wherein A is H or $CH_3$, B is $(CH_2)_m$, m is 2-5, Y is nothing or O, w is 0-1, and D is H. Most preferred are 2-phenylethyl methacrylate; 4-phenylbutyl methacrylate; 5-phenylpentyl methacrylate; 2-benzyloxyethyl methacrylate; and 3-benzyloxypropyl methacrylate; and their corresponding acrylates.

Monomers of formula IV are known and can be made by known methods. For example, the conjugate alcohol of the desired monomer can be combined in a reaction vessel with methyl methacrylate, tetrabutyl titanate (catalyst), and a polymerization inhibitor such as 4-benzyloxy phenol. The vessel can then be heated to facilitate the reaction and distill off the reaction by-products to drive the reaction to completion. Alternative synthesis schemes involve adding methacrylic acid to the conjugate alcohol and catalyzing with a carbodiimide or mixing the conjugate alcohol with methacryloyl chloride and a base such as pyridine or triethylamine.

Device materials generally comprise a total of at least about 75%, preferably at least about 80%, of device-forming monomers.

In addition to an absorber of the present invention and a device-forming monomer, the device materials of the present invention generally comprise a cross-linking agent. The cross-linking agent used in the device materials of this invention may be any terminally ethylenically unsaturated compound having more than one unsaturated group. Suitable cross-linking agents include, for example: ethylene glycol dimethacrylate; diethylene glycol dimethacrylate; allyl methacrylate; 1,3-propanediol dimethacrylate; 2,3-propanediol dimethacrylate; 1,6-hexanediol dimethacrylate; 1,4-butanediol dimethacrylate; $CH_2$=$C(CH_3)C(=O)O$—$(CH_2CH_2O)_p$—$C(=O)C(CH_3)$=$CH_2$ where p=1-50; and $CH_2$=$C(CH_3)C(=O)O(CH_2)_tO$—$C(=O)C(CH_3)$=$CH_2$ where t=3-20; and their corresponding acrylates. A preferred cross-linking monomer is $CH_2$=$C(CH_3)C(=O)O$ $(CH_2CH_2O)_p$—$C(=O)C(CH_3)$=$CH_2$ where p is such that the number-average molecular weight is about 400, about 600, or about 1000.

Generally, the total amount of the cross-linking component is at least 0.1% by weight and, depending on the identity and concentration of the remaining components and the desired physical properties, can range to about 20% by weight. The preferred concentration range for the cross-linking component is 1-5% for small, hydrophobic compounds with molecular weights typically less than 500 Daltons, and 5-17% (w/w) for larger, hydrophilic compounds with molecular weights typically between 500-5000 Daltons.

Suitable polymerization initiators for device materials containing a UV/Vis is absorber of the present invention include thermal initiators and photoinitiators. Preferred thermal initiators include peroxy free-radical initiators, such as t-butyl (peroxy-2-ethyl)hexanoate and di-(tert-butylcyclohexyl) peroxydicarbonate (commercially available as Perkadox® 16 from Akzo Chemicals Inc., Chicago, Ill.). Initiators are typically present in an amount of about 5% (w/w) or less. Because free-radical initiators do not become chemically a part of the polymers formed, the total amount of initiator is customarily not included when determining the amounts of other ingredients.

The device materials containing a UV/Vis absorber of the present invention optionally also contain a reactive colorant. Suitable reactive blue-light absorbing compounds include those described in U.S. Pat. No. 5,470,932. Blue-light absorbers are typically present in an amount from about 0.01-0.5% (weight).

In addition to the UV/Vis is absorber of Formula I, a device-forming monomer, a cross-linking agent, and optionally a UV absorber or other visible light absorber, the materials of the present invention may also contain other ingredients, including but not limited to agents to reduce tack or glistenings. Examples of agents to reduce tack are those disclosed in U.S. Publication Nos. 2009/0132039 A1 and 2009/0137745 A1. Examples of agents to reduce glistenings are those disclosed in U.S. Publication Nos. 2009/0093604 A1 and 2009/0088544 A1.

IOLs constructed of the materials of the present invention can be of any design capable of being rolled or folded into a small cross section that can fit through a relatively smaller incision. For example, the IOLs can be of what is known as a one piece or multipiece design, and comprise optic and haptic components. The optic is that portion which serves as the lens. The haptics are attached to the optic and hold the optic in its proper place in the eye. The optic and haptic(s) can be of the same or different material. A multipiece lens is so called because the optic and the haptic(s) are made separately and then the haptics are attached to the optic. In a single piece lens, the optic and the haptics are formed out of one piece of material. Depending on the material, the haptics are then cut, or lathed, out of the material to produce the IOL.

In addition to IOLs, the materials of the present invention are also suitable for use in other ophthalmic devices, such as contact lenses, keratoprostheses, and corneal inlays or rings.

The invention will be further illustrated by the following examples, which are intended to be illustrative, but not limiting.

EXAMPLE 1

Synthesis of 4-allyl-2-(hydroxymethyl)-6-methoxyphenol. In a 2 liter round bottom flask equipped with nitrogen inlet and magnetic stirrer was dissolved eugenol, 99% (Alfa Aesar) in a solution comprised of 286 g NaOH in 1.2 L water at 0° C. A solution of formaldehyde (828 g, 10.2 mol), 37 wt. % solution in water, A.C.S. reagent (Sigma-Aldrich) was added dropwise to the stirring solution. The mixture was stirred under nitrogen at ambient temperature for 4 hours and then 55° C. for 20 h. The reaction mixture was poured into 1 L ethyl acetate and washed with 1 N HCl and deionized water. The crude product containing ~30 mol % unreacted eugenol was used in the next step without further purification.

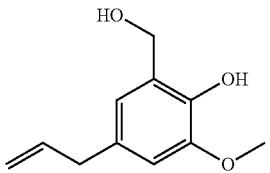

EXAMPLE 2

Synthesis of 4-allyl-2-((5-chloro-2-nitrophenyl)diazenyl)-6-methoxy-phenol. In a 1000 ml 3-neck round bottom flask equipped with a magnetic stirrer was added 5-chloro-2-nitroaniline (Acros Organics, 29.9 g, 173 mmol), concentrated aqueous HCl (36.5-38.0%, 75 ml), 150 ml deionized water, and 150 ml absolute ethanol. The suspension was cooled to −10° C. and a solution of sodium nitrite (Sigma-Aldrich, 12.7 g, 184 mmol) in 50 ml water was added dropwise over 30 minutes at −10° C. The reaction mixture was stirred for 1 hour and 324 mg sulfamic acid (Aldrich) was added. After 10 minutes of stirring the solids were filtered out and the cold solution was set aside. A NaOH solution was prepared by dissolving NaOH (Aldrich, 37.7 g, 944 mmol) in 120 ml deionized water. Approximately one fourth of the sodium hydroxide solution was added dropwise to a solution of 4-allyl-2-(hydroxymethyl)-6-methoxyphenol from Example 1 in 100 ml water and 300 ml absolute ethanol. The diazonium mixture and remaining NaOH solution were concurrently added dropwise over 1 hr to the 4-allyl-2-(hydroxymethyl)-6-methoxyphenol solution at −10° C. The resulting dark mixture was stirred at 0° C. for 1 hour and ambient temperature for 2 hours. The contents were poured into 3 liters deionized water and the pH was adjusted to 5 using 1 N HCl. The solid was filtered and dried at 50° C. for 64 hours using P$_2$O$_5$ drying agent to afford 28 g (46%) that was used in the next step without further purification.

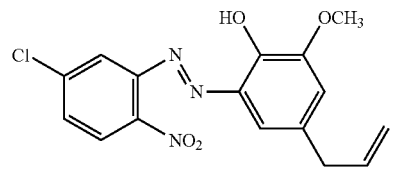

EXAMPLE 3

Synthesis of 4-allyl-2-(5-chloro-2H-benzo[d][1,2,3]triazol-2-yl)-6-methoxy-phenol. In a 1 L round bottom flask equipped with a magnetic stirrer, addition funnel, powder addition funnel, and nitrogen inlet was added 4-allyl-2-((5-chloro-2-nitrophenyl)diazenyl)-6-methoxyphenol (27.9, 80.2 mmol) from Example 2 and 300 ml absolute ethanol. NaOH (19.3 g, 483 mmol) was dissolved in 140 ml deionized water and approximately one-fourth by volume was added dropwise to the reaction mixture. The reaction mixture was heated to 80° C. and formamidinesulfinic acid (Aldrich, 26.0 g, 241 mmol) was added slowly and concurrently with the remaining sodium hydroxide solution over 30 minutes. The reaction mixture was poured into 3 L deionized water and acidified to pH 4 with 1 N HCl. The yellow solid was dried for 20 hours at 42° C. and then purified by dissolving in hot toluene and then filtering out the dark impurities. The filtrate was concentrated down and purified via recrystallizions in ethanol and diethyl ether to give the pure product (5 g, 20%). $^1$H NMR (CDCl$_3$) delta: 11.03 (s, 1H, phenol OH), 7.94 (s, 1H, Ar—H benzotriazole ring, 4-position), 7.89 (m, 1H, Ar—H benzotriazole ring, 7-position), 7.80 (s, 1H, Ar—H phenol, 5-position), 7.44 (m, 1H, Ar—H benzotriazole ring, 6-position), 6.81 (s, 1H, Ar—H phenol, 3-position), 6.00 (m, 1H, HC=CH$_2$), 5.16 (m, 2H, HC=CH$_2$), 3.97 (s, 3H, CH$_3$O), 3.43 (d, 2H, Ar—CH$_2$).

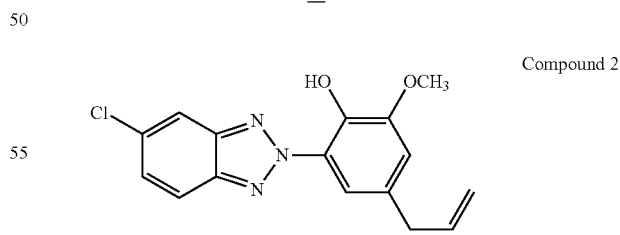

Compound 2

Figure 3:
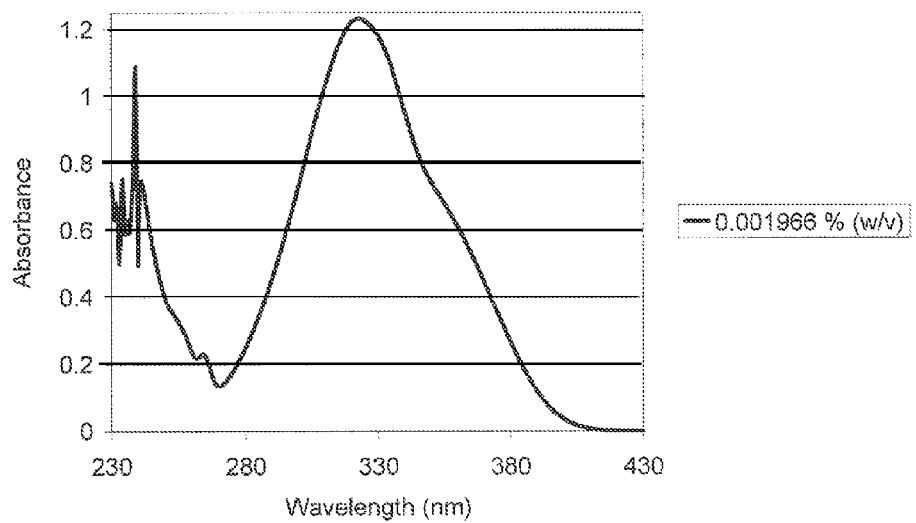
FIG. 3 shows the absorbance curve for Compound 2.

A simple absorbance plot of Compound 2 (0.002% w/v in CHCl$_3$) was generated via UV/Vis is spectroscopy using a 10 mm quartz cell. The results are shown in FIG. 3.

EXAMPLE 4

Transmittance curves for Compound 2 at various concentrations were to generated by UV/Vis is spectroscopy. Compound 1 was dissolved in chloroform and evaluated in a PerkinElmer Lambda 35 UV/Vis is spectrometer. The results are shown in FIG. 1.

EXAMPLE 5

Polymer Test Samples Containing Compound 2

Compound 1 from Example 3 was formulated as shown in Table 1. All components were vortex mixed in a 40 ml glass vial, degassed with nitrogen, and then syringe filtered using a 0.2 micron Teflon filter into ~1 mm deep rectangular polypropylene molds. Samples were thermally cured at 90° C. for 1 hour and 110° C. for 2.5 hours and then extracted in refluxing acetone for 6 hours with fresh solvent replacement every 90 minutes.

TABLE 1

| Component | Example (% w/w) 5 |
|---|---|
| Compound 2 | 2.5 |
| BzA | 82.7 |
| BzMA | 9.9 |
| polyPEG | 3.2 |
| BDDA | 1.7 |
| AIBN | 1.0 |

BzA = benzyl acrylate
BzMA = benzyl methacrylate
polyPEG = 4000 molecular weight polymer of polyethylene glycol(550)-methacrylate (polyPEG macromonomer)
BDDA = 1,4-butanediol diacrylate
AIBN = 2,2'-Azobis(2-methylpropionitrile)

The polymer test samples were tested for % extractables, refractive index, and equilibrium water content (35° C.) as shown in Table 2. The test samples were also examined for glistenings after equilibrating test samples at 45° C. for 20 hours followed by cooling to 22° C. Tensile properties were measured and values are reported in Table 3.

TABLE 2

| Example | % Extractables | EWC (35° C.) (%) | R.I. (35° C.) | Glistenings Per Test Sample |
|---|---|---|---|---|
| 5 | 4.8 ± 0.2 | 1.1 | 1.5605 | [1]0 to very few |

[1]Sample was equilibrated in deionized water for 20 hours at 45° C., then cooled to ambient temperature and inspected by an optical microscope 1-2 hours later

TABLE 3

| Example | Stress At Break (MPa) | Strain At Break (%) | Young's Modulus (MPa) | 25% Secant Modulus (MPa) | 100% Secant Modulus (MPa) |
|---|---|---|---|---|---|
| 5 | 6.1 ± 0.7 | 140 ± 13 | 105 ± 12 | 15.2 ± 1.5 | 4.6 ± 0.3 |

Figure 2:
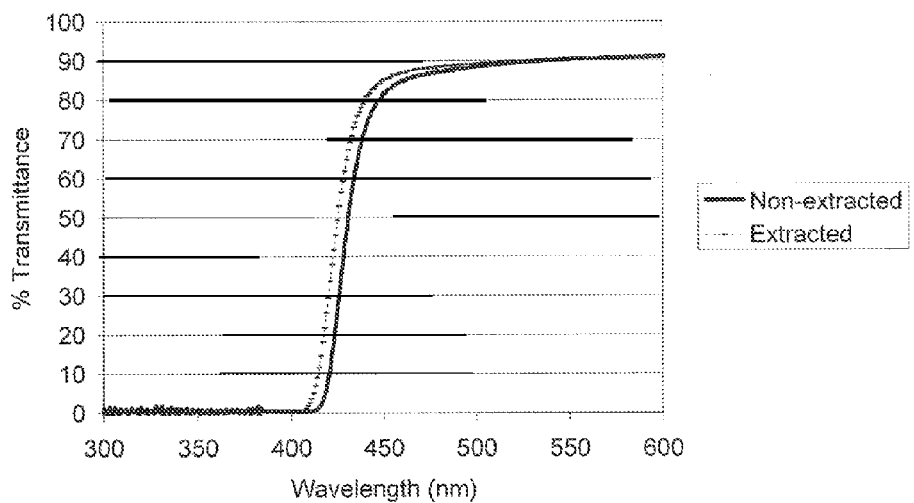
FIG. 2 shows the percent transmittance curves for Compound 2 in a polymeric sample before and after acetone extraction.

UV/Vis is spectra from ~1 mm thick sample sections were collected using a PerkinElmer Lambda 35 UV/Vis is spectrometer. As shown in FIG. 2, the UV/Vis is spectrum of extracted and unextracted test samples for the polymeric material of Example 5 confirms that not all of the UV absorber is covalently incorporated in the polymer network. The relatively high % extractables in Table 2 corroborates these results. This is attributed to the relatively slow reaction kinetics of the propenyl double bond of Compound 1 under the given reaction conditions. Relatively low incorporation of the UV/Vis is absorbers can be easily circumvented by converting the propenyl double bond to a (meth)acrylate group as described above (e.g., Compounds 2 and 3).

EXAMPLE 6

Acrylic IOL Formulations

Compounds 2 was formulated in IOL materials as shown in Table 4. All components were vortex mixed in a 30 ml glass vial, degassed with nitrogen, and then syringe filtered using a 0.2 micron Teflon filter into ~1 mm deep rectangular polypropylene molds. Samples were thermally cured at 70° C. for 1 hour and 110° C. for 2 hours and then extracted in acetone at 50° C. for 6 hours with fresh solvent replacement every 90 minutes.

TABLE 4

| | EXAMPLE % (w/w) | | | |
|---|---|---|---|---|
| Component | 6A | 6B | 6C | 6D |
| Compound 2 | 2.49 | 2.50 | 2.48 | 2.48 |
| PEA | 0 | 0 | 73.1 | 73.0 |
| PEMA | 0 | 0 | 19.9 | 20.0 |
| BzA | 82.7 | 92.9 | 0 | 0 |
| BzMA | 9.92 | 0 | 0 | 0 |
| Secondary alcohol ethoxylate, methacrylic acid ester | 0 | 3.10 | 0 | 3.01 |
| PolyPEGMA | 3.200 | 0 | 3.00 | 0 |
| BDDA | 1.70 | 1.50 | 1.53 | 1.52 |
| AIBN | 1.01 | 0.53 | 0.60 | 0.50 |

PEA = 2-phenylethyl acrylate
PEMA = 2-phenylethyl methacrylate
BzA = benzyl acrylate
BzMA = benzyl methacrylate
BDDA = 1,4-butanediol diacrylate Secondary alcohol ethoxylate,
methacrylic acid ester = methacrylic acid ester of Tergitol ™ NP-70 surfactant (Dow/Union Carbide)
PolyPEGMA = Macromonomer of poly(ethylene glycol) monomethyl ether methacrylate (MW = 550),
Mn (SEC): 4100 Daltons,
Mn (NMR): 3200 Daltons,
PDI = 1.5
AIBN = 2,2'-Azobis(2-methylpropionitrile)

TABLE 5

| | EXAMPLE % (w/w) | | | |
|---|---|---|---|---|
| Component | 6A | 6B | 6C | 6D |
| Compound 4 | 1.49 | 2.00 | 2.48 | 3.00 |
| PEA | 0 | 0 | 73.1 | 73.0 |
| PEMA | 0 | 0 | 19.9 | 19.5 |
| BzA | 83.7 | 93.4 | 0 | 0 |
| BzMA | 9.92 | 0 | 0 | 0 |
| Secondary alcohol ethoxylate, methacrylic acid ester | 0 | 3.10 | 0 | 3.01 |
| PolyPEGMA | 3.200 | 0 | 3.00 | 0 |
| BDDA | 1.70 | 1.50 | 1.53 | 1.52 |
| AIBN | 1.01 | 0.53 | 0.60 | 0.50 |

This invention has been described by reference to certain preferred embodiments; however, it should be understood that it may be embodied in other specific forms or variations thereof without departing from its special or essential characteristics. The embodiments described above are therefore considered to be illustrative in all respects and not restrictive, the scope of the invention being indicated by the appended claims rather than by the foregoing description.

I claim:
1. A benzotriazole compound of the formula

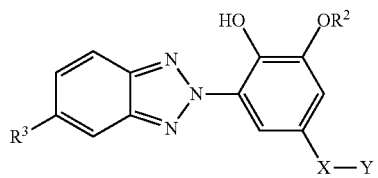

wherein
X=$C_3$-$C_4$ alkenyl, $C_3$-$C_4$ alkyl, $CH_2CH_2CH_2SCH_2CH_2$ or $CH_2CH_2CH_2SCH_2CH_2CH_2$;
Y=nothing if X=$C_3$-$C_4$ alkenyl, otherwise
Y=—O—C(=O)—C($R^1$)=$CH_2$, —O—C(=O)NHCH_2CH_2OC(=O)—C($R^1$)=$CH_2$, or —O—C(=O)NHC($CH_3$)_2($C_6H_4$)C($CH_3$)=$CH_2$;
$R^1$=H, $CH_3$, $CH_2CH_3$, or $CH_2OH$;
$R^2$=$C_1$-$C_4$ alkyl; and
$R^3$=H, $CH_3$, $CH_3O$, F, Cl, Br, I, or $CF_3$.

2. The benzotriazole compound of claim 1, wherein
X=$C_3$-$C_4$ alkenyl, $C_3$-$C_4$ alkyl, or $CH_2CH_2CH_2SCH_2CH_2$;
Y=nothing if X=$C_3$-$C_4$ alkenyl, otherwise Y=—O—C(=O)—C($R^1$)=$CH_2$;
$R^1$=H or $CH_3$;
$R^2$=$C_1$-$C_2$ alkyl; and
$R^3$=$CH_3$, $CH_3O$, F, Cl, or $CF_3$.

3. An intraocular lens comprising a benzotriazole compound of claim 2.

4. The benzotriazole compound of claim 2, wherein the compound is selected from the group consisting of:
2-(3-(3-(5-chloro-2H-benzo[d][1,2,3]triazol-2-yl)-4-hydroxy-5-methoxy-phenyl)propylthio)ethyl methacrylate;
4-allyl-2-(5-chloro-2H-benzo[d][1,2,3]triazol-2-yl)-6-methoxyphenol;
3-(3-(5-chloro-2H-benzo[d][1,2,3]triazol-2-yl)-4-hydroxy-5-methoxyphenyl)-propyl methacrylate;
4-allyl-2-methoxy-6-(5-(trifluoromethyl)-2H-benzo[d][1,2,3]-triazol-2-yl)phenol; and
3-(4-hydroxy-3-methoxy-5-(5-(trifluoromethyl)-2H-benzo[d][1,2,3]triazol-2-yl)phenyl)propyl methacrylate.

5. The benzotriazole compound of claim 4, wherein the compound is 2-(3-(3-(5-chloro-2H-benzo[d][1,2,3]triazol-2-yl)-4-hydroxy-5-methoxy-phenyl)propylthio)ethyl methacrylate.

6. The benzotriazole compound of claim 4, wherein the compound is 3-(4-hydroxy-3-methoxy-5-(5-(trifluoromethyl)-2H-benzo[d][1,2,3]triazol-2-yl)phenyl)propyl methacrylate.

7. An intraocular lens comprising a benzotriazole compound of claim 4.

8. A copolymeric ophthalmic device material formed by copolymerizing a composition comprising a benzotriazole compound of claim 1 and a device-forming monomer selected from the group consisting of acrylic monomers and silicone-containing monomers.

9. The ophthalmic device material of claim 8, wherein the composition comprises from 0.1 to 5% w/w of the benzotriazole compound.

10. The ophthalmic device material of claim 9, wherein the composition comprises from 0.5 to 4% w/w of the benzotriazole compound.

11. The ophthalmic device material of claim 10, wherein the composition comprises from 1 to 3% w/w of the benzotriazole compound.

12. The ophthalmic device material of claim 8, wherein the composition comprises a device-forming monomer of formula [IV]:

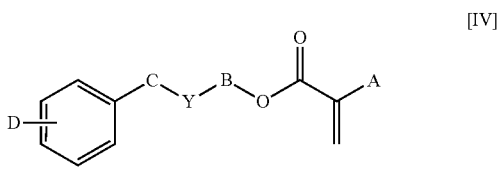

where in formula [IV]:
A is H, $CH_3$, $CH_2CH_3$, or $CH_2OH$;
B is $(CH_2)$, or $[O(CH_2)_2]_z$;
C is $(CH_2)_w$;
m is 2-6;
z is 1-10;
Y is a direct bond, O, S, or NR', provided that if Y is O, S, or NR', then B is $(CH_2)_m$;
R' is H, $CH_3$, $C_{n'}H_{2n'+1}$ (n'=1-10), iso-$OC_3H_7$, $C_6H_5$, or $CH_2C_6H_5$;
w is 0-6, provided that m+w≦8; and
D is H, $C_1$-$C_4$ alkyl, $C_1$-$C_4$ alkoxy, $C_6H_5$, $CH_2C_6H_5$ or halogen.

13. The ophthalmic device material of claim 12, wherein in formula [IV]:
A is H or $CH_3$;
B is $(CH_2)_m$;
m is 2-5;
Y is a direct bond or O;
w is 0-1; and
D is H.

14. The ophthalmic device material of claim 13, wherein the composition comprises a monomer selected from the group consisting of: 2-phenylethyl methacrylate; 4-phenylbutyl methacrylate; 5-phenylpentyl methacrylate; 2-benzyloxyethyl methacrylate; and 3-benzyloxypropyl methacrylate; and their corresponding acrylates.

15. The ophthalmic device material of claim 8, wherein the composition comprises a cross-linking agent.

16. The ophthalmic device material of claim 8, wherein the composition comprises a reactive blue-light absorbing compound.

17. An ophthalmic device comprising the ophthalmic device material of claim 8.

18. The ophthalmic device of claim 17, wherein the ophthalmic device is selected from the group consisting of an intraocular lens; a contact lens; a keratoprosthesis; a corneal inlay; and a corneal ring.

19. An intraocular lens comprising a benzotriazole compound of claim 1.

* * * * *